United States Patent [19]
Burhop et al.

[11] Patent Number: 6,046,170
[45] Date of Patent: Apr. 4, 2000

[54] THERAPEUTIC USE OF HEMOGLOBIN TO TREAT HEAD INJURY

[75] Inventors: Kenneth E. Burhop, Mundelein, Ill.; Steven R. Shackford, Shelburne, Vt.

[73] Assignee: Baxter International, Inc., Deerfield, Ill.

[21] Appl. No.: 09/177,326

[22] Filed: Oct. 22, 1998

Related U.S. Application Data

[63] Continuation of application No. 08/734,296, Oct. 21, 1996, abandoned.

[51] Int. Cl.$^7$ ............................................. A61K 38/00
[52] U.S. Cl. ........................... 514/21; 514/6; 424/529; 435/67.1; 530/385
[58] Field of Search ..................... 514/6, 21; 424/529; 435/69.1; 530/385

[56] References Cited

U.S. PATENT DOCUMENTS

| | | | |
|---|---|---|---|
| 4,529,719 | 7/1985 | Tye | 514/6 |
| 4,908,350 | 3/1990 | Kramer et al. | 514/2 |
| 4,994,444 | 2/1991 | Zikria | 514/60 |
| 5,290,803 | 3/1994 | Abraham et al. | 514/421 |
| 5,382,680 | 1/1995 | Abraham et al. | 562/451 |
| 5,386,014 | 1/1995 | Nho et al. | 530/385 |
| 5,439,882 | 8/1995 | Feola et al. | 514/6 |
| 5,510,464 | 4/1996 | Przybelski | 530/385 |

FOREIGN PATENT DOCUMENTS

| | | |
|---|---|---|
| 660257 | 9/1993 | Australia. |
| 0140640 | 5/1985 | European Pat. Off.. |
| 9629346 | 9/1996 | WIPO. |

OTHER PUBLICATIONS

Chappell et al., Hemodilution with Diaspirin Cross–Linked Hemoglobin Lowers Intracranial Pressure, Improves Cerebral Perfusion Pressure and Reduces Fluid Requirement Following Head Injury and Shock, Surgical Forum, vol. 46, No. 0, pp. 569–571, 1995.
Schell et al., Hemodilution with Diaspirin Hemoglobin During Cerebral Ischemia in Rats: The Effect on Cerebral Blood Flow, p. 197.
Byrne et al., Investigation of the Vasoconstrictor Action of Subarachnoid Haemoglobin in the Pig Cerebral Circulation in vivo, Br. J. Pharmacol, vol. 97, pp. 669–674, 1989.
Przybelski et al., Cross–Linked Hemoglobin Solution as a Resuscitative Fluid After Hemorrhage in the Rat, J. Lab. Clin. Med., vol. 117, No. 2, pp. 143–151, 1991.
Cole et al., Hemodilution During Cerebral in Rats: Effects Stroma–Free Hemoglobin on Brain Injury, Anesth. Analg., vol. 74, Abstract S50, (1 page), 1992.
Cole et al., Focal Cerebral Ischemia in Rats: Effect of Hypervolemic Hemodilution with Diaspirin Cross–linked Hemoglobin Versus Albumin on Brain Injury and Edema, Anesthesiology, vol. 78, No. 2, pp. 335–342, 1993.
Cole et al., Focal Cerebral Ischemia in Rats: Effect of Hemodilution with α–α Cross–Linked HemogloDin on Brain Injury and Edema, The Canadian Journal of Neurological Sciences, vol. 20, No. 1, pp. 30–36, 1993.
Muizelaar et al., Effect of Hematocrit Variations on Cerebral Blood Flow and Basilar Artery Diameter in vivo, The American Physiological Society, pp. H949–954, 1992.
Rebello et al., Diaspirin Crosslinked Hemoglobin Reverses the Reduction in Cerebral Blood Flow Induced by Central Endothelin (ET), The FASEB Journal, vol. 8, No. 4, Part II Abstract 4802, p. A828, 1994.
Sharma et al., Regional Circulatory and Systemic Hemodynamic Effects of Diaspirin Cross–Linked hemoglobin in the Rat, Art. Cells, Blood Subs., and Immob. Biotech., vol. 22, No. 3, pp. 593–602, 1994.
Schell et al., Hemodilution During Cerebral Ischemia in Rats: Effects of Stroma–Free Hemoglobin on Blood Flow, Anesth. Analg., vol. 74, Abstract S262, (1 page), 1992.
Dorland's Illustrated Medical Dictionary, Edition 28, p. 843.
Cecil Textbook of Medicine, $20^{th}$ Edition, volume 1, Sections 419.1 and 437, pp. 2063–2073, 2135–2139 (1996).
Estep, et al., Diaspirin Crosslinked Hemoglobin (DCLHb): A Review of Cardiovascular and Pharmacologic Properties, ISBS 1993 Program and Abstracts (1 page).
Foley, et al., Cytotoxic Effects of Bloody Cerebrospinal Fluid on Cerebral Endothelial Cells in Culture, Journal of Neurosurgery, vol. 81, pp. 87–92, 1994.
Katsuyama et al., Nitric Oxide Mediates the Hypertensive Response to a Modified Hemoglobin Solution (DCLHb) in Rats Art. Cells, Blood Subs., and Immob. Biotech., vol. 22, No. 1, pp. 1–7, 1994.
Marzatico, et al., Effects of Nicardipine Treatment on Na+–K+ ATPase and Lipid Peroxidation After Experimental Subarachnoid Hemorrhage, Acta Neurochir, vol. 108, pp. 128–133, 1991.

*Primary Examiner*—Bennett Celsa
*Attorney, Agent, or Firm*—Senniger, Powers, Leavitt & Roedel

[57] ABSTRACT

A method for treating head injury in a mammal is provided. The method comprises administering to a mammal having a head injury an effective amount of a hemoglobin preparation. A preferred hemoglobin for use in the method is diaspirin crosslinked hemoglobin.

23 Claims, No Drawings

THERAPEUTIC USE OF HEMOGLOBIN TO TREAT HEAD INJURY

This application is a continuation of Ser. No. 08/734,296 (Oct. 21, 1996), now abandoned.

BACKGROUND OF THE INVENTION

The present invention relates to the treatment of head injury. More specifically, the present invention relates to the use of hemoglobin preparations to reduce elevated intracranial pressure and increase depressed cerebral blood flow and cerebral perfusion pressure in head injured patients.

DESCRIPTION OF RELATED ART

Head injury is one of the most common causes of death and disability in the Western world (Alexander et al. (1993) *Advanced Trauma Life Support Course for Physicians,* American College of Surgeons Committee on Trauma; Anderson et al. (1980) *J. of Trauma* 53:S1-543). Prompt and effective treatment of head injury significantly contributes to effective recovery. Delays in initial resuscitation, extrication, and transport of injured victims exacerbate the effects of the initial head injury due to secondary insults such as hypoxia, hypotension, and pyrexia to the damaged brain (Miller et al. (1982) *J. Royal Coll. Surg. Edinb.* 27:292–298; Jones et al. (1994) *J. Neurosurg. Anaesth.* 6:4–14). These events can contribute to brain swelling and intracranial hypertension, causing a potentially deleterious reduction in brain perfusion.

After airway, breathing and circulation are established, and hematomas, when present, are surgically removed, care must be taken to prevent secondary insults. Brain swelling often occurs immediately after head trauma and may occur well after the trauma because of delayed traumatic cell damage. Elevated intracranial pressure is an often encountered secondary insult contributing to patient morbidity and mortality (Jones et al. (1994) *J. Neurosurg. Anaesth.* 6:4–14). As noted by Marmarou et al. ((1991) *J. Neurosurg.* 75:21–27), post injury raised ICP (ICP>20 mmHg) occurs in over 70% of severely head injured patients. Most of these patients suffer diffuse brain swelling, with the majority of the raised ICP in these patients being caused by vascular mechanisms (Marmarou et al. (1987) *J. Neurosurg.* 66:883–890).

In the absence of surgically remediable causes, intracranial pressure increases can be treated by a variety of different treatments to reduce ICP while preventing hypoperfusion. These include mild hypocapnia, oxygenation, and pharmacological control of intracranial hypertension. Mild hypocapnia results in vasoconstriction, which reduces the contribution of cerebral blood volume to increased ICP. Pressor agents, such as noradrenaline, artificially elevate blood pressure, encouraging perfusion. Osmotic diuretic treatments can reduce edema associated with the disruption of cerebral tissue. Investigations are currently being carried out on the utility of blockers of the inflammatory cascade in controlling ICP after head injury.

Many of these treatments are accompanied by various problems. Treatments that reduce cerebral vessel diameter may not be effective because they may deprive the damaged brain of vital perfusion. Osmotic diuretic methods reduce brain edema, increase serum osmolarity, and can result in renal toxicity.

The range of agents effective in treating raised ICP and reduced cerebral perfusion pressure secondary to head injury is presently limited, and a need exists for new therapies to treat these conditions in brain injured patients.

SUMMARY OF THE INVENTION

Among the objects of the invention, therefore, may be noted the provision of a hemoglobin solution for treating a head injury in a mammal; the provision of a method for lowering elevated intracranial pressure associated with head injury; and the provision of a method for elevating depressed cerebral perfusion pressure associated with head injury.

The present invention provides a method for treating head injury in a mammal, comprising administering to a mammal suffering from a head injury an effective amount of a hemoglobin preparation. Hemoglobin is this preparation can be chemically modified to prevent intra- or intermolecular dissociation.

In another aspect, the method further comprises administering to said mammal at least one additional effective amount of a hemoglobin preparation after initial administration of said effective amount of a hemoglobin preparation.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein are herein incorporated by reference in their entirety.

In the present invention, a hemoglobin preparation is administered in a therapeutically effective amount to a mammal, including a human patient, who has suffered head injury as a result of, for example, trauma, accident, infection, or surgery. The beneficial effects resulting from this treatment include a reduction in elevated intracranial pressure and elevation of depressed cerebral perfusion pressure.

Useful doses of hemoglobin for the treatment of head injuries according to the present invention are those that are effective in reducing or eliminating the increase in intracranial pressure and/or decrease in cerebral perfusion pressure frequently observed following head injury.

These results can be achieved with hemoglobin doses effective in reducing intracranial pressure and elevating cerebral perfusion pressure in the range of from about 10 mg/kg body weight to about 5,500 mg/kg body weight, more preferably from about 50 mg/kg body weight to about 2,500 mg/kg body weight, and most preferably from about 75 mg/kg body weight to about 1,500 mg/kg body weight.

Administration of an effective amount of hemoglobin to reduce or eliminate increases in ICP associated with head injury and/or increase CPP by the method of the present invention can be carried out parenterally, for example by intravenous or intraarterial injection, infusion, or arterial cannulization (in appropriate clinical circumstances), peritraumatically or perioperatively. Such effective amount can be administered in a single dose, or in a series of multiple subdoses. The single dose or each of said multiple subdoses can be administered by slow continuous infusion.

Administration of hemoglobin to control increases in ICP and/or to increase CPP in head-injured patients can be via such single dose, or multiple subdoses, given within about one minute to about 48 hours after occurrence of the injury or surgery, more preferably within about one minute to about 12 hours, most preferably within about one minute to about 3 hours. After initial administration of an effective amount of a hemoglobin preparation, at least one additional effective amount of a hemoglobin preparation can be administered in the same manner as described herein for the initial dose.

As used herein, the term "hemoglobin" includes all oxygen-carrying proteins containing globin or globin-like polypeptides and heme, and being capable of transporting and releasing oxygen to cells, tissues or organs when introduced into the blood stream of a mammal in a physiologically compatible carrier. The term "hemoglobin" includes all naturally- and non-naturally-occurring hemoglobin. The term "hemoglobin preparation" includes hemoglobin in a physiologically compatible carrier or lyophilized hemoglobin reconstituted with a physiologically compatible carrier, but does not include whole blood, red blood cells or packed red blood cells.

Naturally-occurring hemoglobin includes any hemoglobin identical to hemoglobin naturally existing within a cell. Naturally-occurring hemoglobin is predominantly wild-type hemoglobin, but also includes naturally-occurring mutant hemoglobin. Wild-type hemoglobin is hemoglobin most commonly found within natural cells. Wild-type human hemoglobin includes hemoglobin A, the normal adult human hemoglobin having two α- and two β-globin chains. Mutant hemoglobin has an amino-acid sequence that differs from the amino-acid sequence of wild-type hemoglobin as a result of a mutation, such as a substitution, addition or deletion of at least one amino acid. Adult human mutant hemoglobin has an amino-acid sequence that differs from the amino-acid sequence of hemoglobin A. Naturally-occurring mutant hemoglobin has an amino-acid sequence that has not been modified by humans. The naturally-occurring hemoglobin of the present invention is not limited by the methods by which it is produced. Such methods typically include, for example, erythrocytolysis and purification, recombinant production, and protein synthesis.

Non-naturally-occurring hemoglobin includes mutant hemoglobin having an amino-acid sequence different from the amino-acid sequence of hemoglobin naturally existing within a cell, and chemically-modified hemoglobin. Such non-naturally-occurring mutant hemoglobin is not limited by its method of preparation, but is typically produced using one or more of several techniques known in the art, including, for example, recombinant DNA technology, protein synthesis, and other mutation-inducing methods.

Chemically-modified hemoglobin is a natural or non-natural hemoglobin molecule which is bonded to or encapsulated by another chemical moiety. For example, a hemoglobin molecule can be bonded to pyridoxal-5'-phosphate, or other oxygen-affinity-modifying moiety to change the oxygen-binding characteristics of the hemoglobin molecule, to crosslinking agents to form crosslinked or polymerized hemoglobin, or to conjugating agents to form conjugated hemoglobin. Conjugated, polymerized and crosslinked hemoglobins generally exhibit longer intravascular retention times than unmodified hemoglobin.

Several examples of hemoglobin modification technology which can be used in the practice of the present invention have been described in the scientific literature (reviewed by R. M. Winslow (1992) in *Hemoglobin-Based Red Cell Substitutes,* The Johns Hopkins University Press, Baltimore, Md.). Some representative methods of preparing chemically-modified hemoglobin for use in the invention are described below.

Hemoglobin can be modified to improve its oxygen-binding affinity. Reagents that bind to the 2,3-diphosphogylcerate binding site of a hemoglobin molecule, reduce the oxygen affinity of the hemoglobin molecule, and prolong intravascular retention are described in U.S. Pat. Nos. 4,529,719 and 5,380,824 (pyridoxal-5'-phosphate), U.S. Pat. No. 4,600,531 (carboxyl-, phosphonate-, phosphate-, sulfonate- or sulfate-phenyl ester-containing compounds such as mono(3,5-dibromosalicyl)fumarate), U.S. Pat. No. 5,268,500 (arylureido acid compound), U.S. Pat. No. 5,382,680 (2[4-(((benzyl)amino)carbonyl) phenoxy]-2-methyl propionic acids), and U.S. Pat. Nos. 5,290,803 and 5,432,191. In general, any method of preparing or modifying hemoglobin such that the hemoglobin can transport and release oxygen is suitable in the present method. Preferably, the hemoglobin has a $P_{50}$ of between about 20 and about 45 mm Hg.

An encapsulated hemoglobin is hemoglobin surrounded by a material which retains the hemoglobin within the material yet allows smaller molecules to pass through the material to react with hemoglobin and reaction products to pass out of the material. Materials for encapsulating hemoglobin are described in U.S. Pat. No. 4,343,715 (polyurethane, acrylic gels, maleic anhydride polymers, epoxy polymers, glutaronic aldehyde polymers), U.S. Pat. Nos. 5,061,688, 5,217,648 and 5,438,041 (oil emulsion), and U.S. Pat. Nos. 4,322,311, 4,324,683 and 4,390,521 (polymers).

A conjugated hemoglobin is at least one non-hemoglobin molecule covalently or ionically bound to a hemoglobin. In some embodiments, the non-hemoglobin molecule can also form an intermolecular crosslink between hemoglobin molecules. Conjugating materials and methods for preparing hemoglobin conjugates are described in WO 91/07190 (polyalkylene glycol), U.S. Pat. Nos. 4,670,417, 5,091,176, 5,219,564, 5,234,903, 5,312,808 and 5,386,014, WO 94/04193, WO 94/09027 and Japanese Patent Nos. 59-104323 and 61-053223 (polyalkylene oxide), U.S. Pat. Nos. 5,349,001 and 5,405,877 (cyclic imide thione activated polyalkylene oxide), U.S. Pat. No. 4,301,144 (polyalkylene glycol, alkylene glycol copolymers, alcohol-polyalkylene glycol ether copolymers, carboxylic acid-polyalkylene glycol ester copolymers, and amine-polyalkylene glycol derivatives), U.S. Pat. Nos. 4,267,234, 4,267,435 and 4,369,226 (polyglutaraldehyde), Canadian Patent Application No. 2,074,852 (divinyl sulfone), U.S. Pat. No. 4,412,989 (polyether), U.S. Pat. No. 4,377,512 (inulin), U.S. Pat. Nos. 5,079,337 and 5,110,909 (polysaccharide, polyvinyl alcohol, polyvinyl pyrrolidone, polymethacrylate, polypeptide, polyalkylene glycol, hydroxyalkyl starch, and dextran), U.S. Pat. No. 4,920,194 (sulfated glycosaminoglycan fragments, such as heparin), U.S. Pat. No. 4,970,156 (active protein), U.S. Pat. No. 4,336,248 (dialdehyde), U.S. Pat. No. 4,900,780 (hydroxyethyl starch or tetronic polymer), and U.S. Pat. Nos. 4,698,387, 4,935,465, and 5,514,780.

Crosslinked hemoglobin is intramolecularly linked between globin or globin-like protein subunits by a crosslinking agent. A subunit is one globin or globin-like protein of a hemoglobin molecule. Intramolecular crosslinking prevents dissociation of globin or globin-like proteins when hemoglobin is administered in vivo. Hemoglobin A, for example, can dissociate into two α-β globin dimers if the dimers are not crosslinked. Crosslinked hemoglobins and methods for their preparation are described in U.S. Pat. Nos. 4,529,719 and 4,600,531 (α-α linkage using diphenyl ester derivatives such as bis(3,5-dibromosalicyl)fumarate), U.S. Pat. Nos. 4,001,401 and 4,053,590 (α-β globin linkage using halogenated cycloalkanes, diepoxides, and diazobenzidines), U.S. Pat. No. 4,857,636 (aldehyde derived from oligosaccharide), U.S. Pat. No. 5,334,705 (benzenetricarboxylate), WO 94/21682 (β-β globin linkage using di- or trisaccharide), U.S. Pat. Nos. 5,290,919 and 5,387,672 (di- or trivalent compounds), U.S. Pat. No. 5,334,707 (β-β or α-α linkage using acyl phosphate ester), U.S. Pat. No. 5,362,885 and WO 92/09630 (imidoesters, such as dimethyl adipimidate or dimethyl suberimidate), U.S. Pat. No. 5,514,780 (polycarboxylic acid), U.S. Pat. No. 5,399,671 and WO 90/13309 (β-β linkage), and U.S. Pat. No. 4,473,496 (dialdehyde).

A polymerized hemoglobin is intermolecularly linked between hemoglobin molecules. Polymerization generally increases the molecular weight of the hemoglobin, which improves its intravascular half-life. Polymerization agents for preparing polymerized hemoglobin are described in pending U.S. applications Ser. Nos. 08/149,679, 08/173,882, 08/480,593, and 08/473,459, U.S. Pat. No. 4,777,244 (aliphatic dialdehyde), U.S. Pat. No. 5,349,054 (benzenepentacarboxylate), WO 94/14460 (transglutaminase), and EP 201618 (glutaraldehyde).

Hemoglobins can also be modified by a combination of the methods described above, for example, as described in Japanese Patent Nos. 59-089629, 59-103322, and 59-104323 (pyridoxal-5'-phosphate modification and polyethylene glycol conjugation of hemoglobin), U.S. Pat. No. 5,248,766 (crosslinking and polymerization of tetrameric hemoglobins with oxiranes), U.S. Pat. Nos. 4,650,786, 4,710,488 and 4,900,816 (inositol phosphate aldehyde modification and polysaccharide conjugation of hemoglobin), U.S. Pat. Nos. 5,189,146 and 5,364,932 (di- or polyaldehydes for intra- and intermolecular crosslinking), EP 361719 (pyridoxylation, dicarboxylic acid halo-ester crosslinking, and polymerization), WO 90/13309 (pyridoxal-5-phosphate derivative for intramolecular crosslinking and glutaraldehyde for polymerization), U.S. Pat. No. 5,439,882 (periodate-oxidized ATP intramolecular crosslinking and periodate-oxidized adenosine polymerization), U.S. Pat. Nos. 4,826,811 and 5,194,590 (pyridoxylation and glutaraldehyde polymerization), and U.S. Pat. No. 4,529,719 (intramolecularly crosslinked with diaspirin ester and pyridoxylated).

Recombinantly-produced hemoglobin is produced by recombinant DNA methodologies, for example, by site-directed mutagenesis, gene fusion, or transfecting a genetically engineered plasmid into a microorganism such as a bacterium or yeast, a cultured cell such as an insect cell, a mammalian cell, or plant cell, a transgenic plant, a transgenic animal, or any other host cell or organism, where the plasmid includes a nucleic acid polymer (e.g., cDNA) which encodes a globin protein, a fusion protein, or a protein similar to globin that can reversibly bind oxygen. Recombinant mutant and artificial hemoglobins and their production in cell cultures or fluids is described in U.S. Pat. Nos. 5,449,759 and 5,028,588, and in WO 88/09179, AU 614525, GB 2234749 B, and EP 358708 B1. Di-α and di-β globin-like polypeptides and other hemoglobin variants produced in bacteria and yeast, and other fused hemoglobins, are described in WO 90/13645, WO 91/16349, EP 561245 A1, and AU 614525. Non-natural multimeric hemoglobin-like proteins are described in WO 93/09143. Production and recovery of human hemoglobin from transgenic pigs are described in WO 92/22646, WO 93/25071, and WO 95/04744. Methods for the preparation and purification of hemoglobin derived from erythrocyte and non-erythrocyte cells are described in WO 92/22646, WO 93/25071, WO 95/04744, WO 95/14038, and WO 96/15151.

Hemoglobins useful in the methods of the present invention are also free of pyrogens, toxins and other contaminants. Pyrogen-free hemoglobin is hemoglobin that is absolutely free of fever-producing contaminants, or hemoglobin that contains amounts of fever-producing contaminants that are physiologically acceptable to humans or other mammals to which the hemoglobin will be administered. Bacterial endotoxins contaminate hemoglobin derived from erythrocytes. The endotoxins are released when erythrocytes are disrupted to obtain hemoglobin. Recombinant hemoglobin produced in non-erythrocyte host cells such as bacteria can also become contaminated with cellular components such as proteins, toxins, or polysaccharides that can elicit toxic or pyrogenic responses when administered to mammals (Rietschel et al. (1992) *Scientific American* 267:54–61; Suffredini et al. (1989) *New Eng. J. Med.* 321:280–287).

Hemoglobins for use in the present invention are also stroma-free. Stroma, the insoluble cell membrane fragments that contaminate hemoglobin derived from lysed erythrocytes, is toxic and has been reported to cause dyspnea, bronchospasm, hypotension, arrhythmia, disseminated intravascular coagulation, activation of complement, and renal, myocardial, and hepatic changes associated with ischemia and acute inflammation (Feola (1988) *Surgery, Gynecology & Obstetrics* 166:211–222; MacDonald et al. (1988) *F.A.S.E.B. J.* 2(6) Abstr. 8217; Stone et al. (1979) *Surgery, Gynecology & Obstetrics* 149:874–876; Rabiner et al. (1967) *J. Exp. Med.* 126:1127–1142. For purposes of the present invention, "stroma-free hemoglobin" is hemoglobin, as defined herein, that is either absolutely free of stroma, or that contains stroma at levels that are physiologically acceptable (i.e., do not cause adverse side effects) in a human or other mammal. Stroma-free hemoglobin that is absolutely free of stroma includes recombinant hemoglobin produced in a non-erythrocyte. Stroma-free hemoglobin that contains stroma at physiologically acceptable levels includes, for example, purified hemoglobin derived from erythrocytes.

The hemoglobin can be dialyzed or exchanged by ultrafiltration into a physiologically acceptable solution preferably to between about 1 and about 20 g/dl hemoglobin. The solution generally comprises a physiologically compatible electrolyte vehicle isosmotic with whole blood and which maintains the reversible oxygen-carrying and delivery properties of the hemoglobin. The physiologically acceptable solution can be, for example, physiological saline, a saline-glucose mixture, Ringer's solution, lactated Ringer's solution, Locke-Ringer's solution, Krebs-Ringer's solution, Hartmann's balanced saline, heparinized sodium citrate-citric acid-dextrose solution, and polymeric plasma substitutes, such as polyethylene oxide, polyvinyl pyrrolidone, polyvinyl alcohol and ethylene oxide-propylene glycol condensates. Such solutions can be administered parenterally, for example by intravenous or intraarterial injection or infusion, without adverse side effects. The hemoglobin can also be lyophilized for storage and reconstituted prior to use. Methods for preparing such solutions or lyophilized powders are known in the art.

A preferred hemoglobin for use in the present method is hemoglobin crosslinked with bis(3,5-dibromosalicyl)- fumarate to create a fumarate crosslink between the two α subunits (DCLHb™, manufactured by Baxter Healthcare, Deerfield, Ill.). This crosslinked hemoglobin is more fully described, together with methods for its preparation, in U.S. Pat. Nos. 4,598,064, 4,600,531, and RE 34,271, omitting the chromatography step. This hemoglobin is preferably manufactured under the conditions disclosed in U.S. Pat. Nos. 4,831,012, 4,861,867, 5,128,452 and 5,281,579 and U.S. patent application Ser. No. 07/207,346.

In practice, a preferred DCLHb™ solution, manufactured by Baxter Healthcare Corporation and useful in the present invention, contains 10 g/dl of modified tetrameric hemoglobin in a balanced electrolyte solution. The product is prepared from units of human red cells from volunteer donors which have been tested and found negative for HbsAg, HIV-1 and 2, and HCV. During manufacture, the red cells are osmotically lysed to release hemoglobin. After ultrafiltration, the stroma-free hemoglobin is reacted with the diaspirin crosslinking agent to produce a stabilized tetrameric hemoglobin having a fumaryl moiety linking the two α subunits. After crosslinking, the reaction mixture is heated to effect viral deactivation and precipitate extraneous proteins. The precipitate is removed by filtration. The DCLHb™ is then concentrated and diafiltered into a physiologic electrolyte vehicle. The resulting solution is isosmotic with whole blood, hyperoncotic (approximately 40 torr), and has the composition shown in Table 1.

TABLE 1

Chemical Assay of 10% Diaspirin Cross-linked Hemoglobin Solution

| | |
|---|---|
| Hemoglobin content | 10.2 g/dl |
| Methemoglobin | 0.7 g/dl |
| $P_{50}$ (37° C.) | 32.0 mmHg |
| Oncotic pressure | 42.7 mmHg |
| Osmolality | 290 mOsm/kg |
| Viscosity | 1.3 centistokes |
| pH | 7.50 |
| $Na^+$ | 140 mEq/L |
| $K^+$ | 5.0 mEq/L |
| $Ca^{++}$ | 2.2 mEq/L |
| $Mg^{++}$ | 1.0 mEq/L |
| $Cl^-$ | 115 mEq/L |
| Lactate | 30 mEq/L |

The following non-limitative example illustrates the effectiveness of the method of the present invention.

EXAMPLE 1

Treatment of Head Injury by Hemodilution With Diaspirin Crosslinked Hemoglobin

The purpose of this experiment was to determine the effects of hemodilution on intracranial pressure, cerebral perfusion pressure, and fluid requirement in a porcine model of brain injury by comparing resuscitation with DCLHb™ to standard resuscitation using Ringer's lactate and blood.

Swine (42±6 kg) underwent anesthesia and instrumentation to measure mean arterial pressure (MAP), hemoglobin concentration (Hb), intracranial pressure (ICP), cerebral perfusion pressure (CPP), cerebral blood flow (CBF; $H_2$ clearance), and total fluid requirements. Cerebral oxygen delivery ($cO_2$del) was calculated (CBF×arterial $O_2$ content). Animals received a focal cryogenic brain injury. After focal cryogenic brain injury, the animals were hemorrhaged to a MAP of 50 torr. They were then randomized to receive a bolus of either 4 cc/kg of Ringer's Lactate (RL) (n=6) or DCLHb™ (n=6) to maintain MAP. The group receiving Ringer's Lactate also received blood, which was recovered from the animals during hemorrhage ("shed blood"), one hour after hemorrhage in the form of packed red blood cells. The group receiving DCLHb™ received shed blood only if the hemoglobin concentration measured as described above dropped below five g/dl. Variables were measured at baseline (BL), five minutes following the creation of the cryogenic brain injury, 45 minutes after the beginning of hemorrhage (H45), and 1, 3, 6, 12, and 24 hours following resuscitation.

As shown in Table 2, at 1 hour following resuscitation, the group receiving DCLHb™ had a greater MAP and CPP ($p<0.05$). By three hours following resuscitation, the group receiving DCLHb™ had a lower Hb concentration, which was persistent. ICP was significantly lower in the group receiving DCLHb™ at 1 and 3 hours following resuscitation. The volume of fluid required to maintain hemodynamic stability 24 hours after injury was significantly lower in the group receiving DCLHb™ than in the group receiving Ringer's Lactate. No statistically significant difference in regional CBF in the lesioned hemisphere was observed between the groups. Despite a significantly lower Hb concentration in the group receiving DCLHb™, cerebral oxygen delivery was not significantly different from that in the group receiving Ringer's Lactate at any time.

The increased CPP, lower ICP, and lower fluid requirement observed in the group receiving DCLHb™ demonstrate that hemodilution with a hemoglobin preparation can be beneficial in the early management of head injury in mammals.

TABLE 2

| Variable | Group | BL | H45 | 1 Hr. | 3 Hr. | 12 Hr. | 24 Hr. |
|---|---|---|---|---|---|---|---|
| | | | | Study Period (Mean ± SEM) | | | |
| MAP, torr | RL | 98 ± 8 | 49 ± 2 | 82 ± 2 | 90 ± 4 | 90 ± 4 | 85 ± 4 |
| | DCLHb | 98 ± 2 | 50 ± 3 | 95 ± 5* | 96 ± 4 | 91 ± 3 | 97 ± 4* |
| Hb, g/dl | RL | 10 ± 0.2 | 10 ± 0.3 | 7 ± 0.1 | 12 ± 0.3 | 11 ± 0.3 | 10 ± 0.4 |
| | DCLHb | 10 ± 0.7 | 9 ± 0.3 | 9 ± 0.2* | 8 ± 0.4* | 7 ± 0.6* | 6 ± 0.3* |
| ICP, torr | RL | 7 ± 1 | 3 ± 2 | 12 ± 2 | 13 ± 1 | 15 ± 3 | 13 ± 3 |
| | DCLHb | 4 ± 1 | 3 ± 1 | 7 ± 1* | 9 ± 1* | 10 ± 2 | 8 ± 2 |
| CPP, torr | RL | 91 ± 8 | 46 ± 1 | 70 ± 2 | 78 ± 5 | 75 ± 5 | 72 ± 4 |
| | DCLHb | 93 ± 2 | 45 ± 4 | 88 ± 6* | 84 ± 5 | 77 ± 5 | 85 ± 4 |
| CBF-L, ml/100 g/min | RL | 63 ± 8 | 38 ± 4 | 54 ± 8 | 41 ± 9 | 52 ± 8 | 58 ± 9 |
| | DCLHb | 49 ± 7 | 31 ± 8 | 34 ± 8 | 36 ± 8 | 43 ± 12 | 55 ± 13 |

TABLE 2-continued

| Variable | Group | BL | H45 | 1 Hr. | 3 Hr. | 12 Hr. | 24 Hr. |
|---|---|---|---|---|---|---|---|
| TFL, cc | RL DCLHb | | | | | | 15,465 ± 897 10,654 ± 505* |

*P < 0.05, Student's t-test, RL vs. DCLHb.
BL indicates baseline; MAP, mean arterial pressure; Hb, hemoglobin; ICP, intracranial pressure; CPP, cerebral perfusion pressure; CBF-L, cerebral blood flow-lesion side; TFL, total fluid requirement.

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A method for reducing elevated intracranial pressure in a mammal following a head injury, comprising administering to a mammal having elevated intracranial pressure resulting from said head injury an amount of a stroma-free hemoglobin preparation effective in decreasing elevated intracranial pressure, wherein said stroma-free hemoglobin is selected from the group consisting of cross linked hemoglobin, conjugated hemoglobin, encapsulated hemoglobin, recombinantly-produced hemoglobin, and polymerized hemoglobin.

2. The method of claim 1, wherein said head injury is a result of an event selected form the group consisting of trauma and accident.

3. The method of claim 1, wherein said mammal is a human.

4. The method of claim 1, wherein said stroma-free hemoglobin preparation is a solution containing intramolecularly-crosslinked hemoglobin.

5. The method of claim 4, wherein said stroma free hemoglobin exhibits increased oxygen binding affinity within a range of $P_{50}$ values between about 20 and about 45 mm Hg.

6. The method of claim 1, wherein said effective amount of stroma free hemoglobin preparation contains from about 10 milligrams hemoglobin per kilogram body weight to about 5,500 milligrams hemoglobin per kilogram body weight.

7. The method of claim 1, wherein said effective amount of stroma free hemoglobin preparation contains from about 50 milligrams hemoglobin per kilogram body weight to about 2,500 milligrams hemoglobin per kilogram body weight.

8. The method of claim 1, wherein said effective amount of stroma free hemoglobin preparation contains from about 75 milligrams hemoglobin per kilogram body weight to about 1,500 milligrams hemoglobin per kilogram body weight.

9. The method of claim 1, wherein said administering is carried out in a time period in the range of from about one minute to about 48 hours after occurrence of said head injury.

10. The method of claim 1, wherein said administering is carried out in a time period in the range of from about one minute to about 12 hours after occurrence of said head injury.

11. The method of claim 1, wherein said administering is carried out in a time period in the range of from about one minute to about 3 hours after occurrence of said head injury.

12. The method of claim 1, wherein said stroma free hemoglobin preparation is in the form of a physiologically acceptable solution for parenteral administration.

13. The method of claim 12, wherein said physiologically acceptable solution comprises a physiologically compatible electrolyte vehicle isosmotic with whole blood and which maintains the reversible oxygen-carrying and delivery properties of hemoglobin in said hemoglobin preparation.

14. The method of claim 12, wherein said physiologically acceptable solution contains from about 1 g/dl to about 20 g/dl stroma free hemoglobin.

15. The method of claim 1, wherein said administering is carried out by intravenous or intraarterial injection, infusion, or arterial cannulization.

16. The method of claim 1, wherein said effective amount of stroma free hemoglobin preparation is administered in a single dose, or in a series of multiple subdoses.

17. The method of claim 16, wherein said single dose is, or said multiple subdoses are, administered over a period of time in the range of from about one minute to about 48 hours.

18. The method of claim 16, wherein said single dose or each of said multiple subdoses is administered by slow continuous infusion.

19. The method of claim 1, further comprising administering to said mammal at least one additional intracranial pressure-decreasing effective amount of a stroma-free hemoglobin preparation after initial administration of said effective amount of said stroma-free hemoglobin preparation.

20. A method for reducing elevated intracranial pressure in a mammal resulting from a head injury, comprising administering to said mammal having elevated intracranial pressure a stroma-free hemoglobin preparation containing about 10 mg/kg body weight to about 5,500 mg/kg body weight of hemoglobin about one minute to about 48 hours after occurrence of said head injury to decrease elevated intracranial pressure, wherein said stroma-free hemoglobin is selected from the group consisting of cross linked hemoglobin, conjugated hemoglobin, encapsulated hemoglobin, recombinantly-produced hemoglobin, and polymerized hemoglobin.

21. A method for reducing elevated intracranial pressure in a mammal resulting from a head injury, comprising: administering to said mammal having elevated intracranial pressure a stroma-free hemoglobin preparation containing about 10 mg/kg body weight to about 5,500 mg/kg body weight of hemoglobin about one minute to about 48 hours after occurrence of said head injury to decrease elevated intracranial pressure, and subsequently administering to said mammal at least one additional dose of a stroma-free hemoglobin preparation containing about 10 mg/kg body weight to about 5,500 mg/kg body weight of hemoglobin to decrease elevated intracranial pressure, wherein said stroma-free hemoglobin is selected from the group consisting of cross linked hemoglobin, conjugated hemoglobin, encapsulated hemoglobin, recombinantly-produced hemoglobin, and polymerized hemoglobin.

22. The method of claim 20, wherein said mammal is a human.

23. The method of claim 21, wherein said mammal is a human.

* * * * *